(12) United States Patent
Gramnäs

(10) Patent No.: US 7,544,214 B2
(45) Date of Patent: Jun. 9, 2009

(54) ARTIFICIAL MULTI-AXIS KNEE JOINT

(75) Inventor: Finn Gramnäs, Kinna (SE)

(73) Assignee: Ossur HF, Reykjavik (IS)

( * ) Notice: Subject to any disclaimer, the term of this patent is extended or adjusted under 35 U.S.C. 154(b) by 150 days.

(21) Appl. No.: 10/575,963

(22) PCT Filed: Oct. 14, 2004

(86) PCT No.: PCT/SE2004/001475

§ 371 (c)(1),
(2), (4) Date: Jan. 3, 2007

(87) PCT Pub. No.: WO2005/037151

PCT Pub. Date: Apr. 28, 2005

(65) Prior Publication Data

US 2007/0208430 A1   Sep. 6, 2007

(30) Foreign Application Priority Data

Oct. 17, 2003   (SE)   .................... 0302737

(51) Int. Cl.
*A61F 2/74*   (2006.01)
*A61F 2/64*   (2006.01)
(52) U.S. Cl. .............. 623/43; 623/39; 623/44
(58) Field of Classification Search ........... 623/43–44, 623/39
See application file for complete search history.

(56) References Cited

U.S. PATENT DOCUMENTS

| | | | | |
|---|---|---|---|---|
| 4,640,492 A | * | 2/1987 | Carlson, Jr. ............... 251/163 |
| 5,405,407 A | * | 4/1995 | Kodama et al. ............... 623/44 |
| 5,728,173 A | | 3/1998 | Chen |
| 5,888,212 A | * | 3/1999 | Petrofsky et al. ............. 623/24 |
| 5,904,721 A | * | 5/1999 | Henry et al. .................. 623/26 |
| 6,106,560 A | * | 8/2000 | Boender ...................... 623/44 |
| 6,117,177 A | | 9/2000 | Chen et al. |
| D446,304 S | * | 8/2001 | Sawatzki et al. ........... D24/155 |
| 6,517,585 B1 | * | 2/2003 | Zahedi et al. ................ 623/24 |
| 6,997,959 B2 | * | 2/2006 | Chen et al. ................... 623/26 |
| 2003/0195637 A1 | | 10/2003 | Shen |
| 2004/0107008 A1 | * | 6/2004 | Veen ........................... 623/39 |
| 2005/0154473 A1 | * | 7/2005 | Bassett ........................ 623/43 |

FOREIGN PATENT DOCUMENTS

| EP | 0947182 A2 | 6/1999 |
|---|---|---|
| EP | 1166726 B1 | 1/2005 |

* cited by examiner

*Primary Examiner*—Corrine M McDermott
*Assistant Examiner*—Melissa Montano
(74) *Attorney, Agent, or Firm*—Bacon & Thomas, PLLC (57) ABSTRACT

An artificial multi-axis knee joint comprising an upper leg portion and a lower leg portion pivotally connected to each other by a front link for pivoting the front link and the upper leg portion relative to each other around a first geometrical pivot axis, and for pivoting the front link and the lower leg portion relative to each other around a second geometrical pivot axis. A rear link is pivotally connected to the upper leg portion for pivoting the rear link and the upper leg portion relative to each other around a third geometrical pivot axis, and pivotally connected at the other end thereof to the lower leg portion for pivoting the rear link and the lower leg portion relative to each other around a fourth geometrical pivot axis. The knee joint further comprises a further means which is integrated in the front link and the rear link.

17 Claims, 9 Drawing Sheets

PRIOR ART

ARTIFICIAL MULTI-AXIS KNEE JOINT

FIELD OF THE INVENTION

The invention relates to an artificial multi-axis knee joint according to the preamble of claim 1.

BACKGROUND OF THE INVENTION

For artificial legs there are both single- and multi-axis artificial knee joints. This invention is applicable to different types of artificial multi-axis knee joints for artificial legs, such as 4-, 5- and 7-axis knee joints, for the purpose of illuminating, but not restricting the invention, it will hereafter be described how the invention may be used for providing a 4-axis knee joint which has a means for controlling the bending characteristics of the knee joint. In comparison to single-axis knee joints, multi-axis knee joints have the advantage that better ground clearance and thereby improved safety during the use of an artificial leg may be obtained, and furthermore they enable movement while using a less energy-intensive step. Another advantage is that multi-axis knee joints have a higher stability during ground contact of the artificial leg than is the case for single-axis knee joints.

In common with many artificial multi-axis knee joints which are used in artificial legs, in addition to the links included in the knee joint, which links connect the upper and lower leg portions, and which enable pivoting of the upper and lower portions relative to each other, in the knee joint, they also have a mechanism for so-called swing phase control. This means that in use of the knee joint and during movement of the leg in the forward direction together with the subsequent swing in the forward direction of the artificial crus leg, the crus leg can be retarded by means of the bending characteristics of the knee joint to obtain a gentle and controlled motion of the leg when the user moves.

For this purpose an externally arranged hydraulic cylinder is often used which is arranged between the upper and lower leg portions of the knee joint, which hydraulic cylinder has the task of effecting the bending characteristics of the knee joint in such a way that the swinging of the artificial crus leg relative to the thigh leg is damped during the swing phase. The hydraulic cylinder is at one end thereof pivotally connected to the lower leg portion and at the other end thereof pivotally connected to the upper leg portion so that when bending the knee joint, the pivot motion of the knee joint is transmitted to a rectilinear motion of the piston of the hydraulic cylinder. The resistance of the hydraulic cylinder will thus determine the requisite torque for bending the knee joint.

However, previously known knee joints of the current type have a number of drawbacks. These are above all that such a knee joint provided with a hydraulic cylinder takes up a lot more space and further, the weight of the hydraulic cylinder contributes to a lower centre of gravity of the knee joint which is unfavourable during the use of the knee joint. Another disadvantage is that special attachment means are required for arranging the hydraulic cylinder on the knee joint. Furthermore, depending on geometrical conditions, in these knee joints the function of the hydraulic cylinder arranged on the knee joint for retarding the pivot motion of the knee joint is not adapted to the different phases of the movement in an optimal way, or in other words; the hydraulic cylinder gives a relatively high pivot resistance during a part of the walking cycle when the pivot resistance could advantageously be relatively low, and the hydraulic cylinder gives a relatively low pivot resistance, or no resistance at all, during a part of the walking cycle when the pivot resistance could advantageously be relatively high.

THE OBJECT OF THE INVENTION AND SUMMARY OF THE INVENTION

One object of the invention is to reduce at least some of the problems mentioned above associated with such previously known knee joints to a substantial extent.

This object is obtained by a knee joint according to claim 1. By the fact that the controlling means, such as a hydraulic cylinder, is integrated in some of the front link and said at least one rear link, a knee joint taking up less space and not requiring special attachment means for the controlling means may be obtained. Furthermore, it is possible to design the knee joint so that the centre of gravity will have a more suitable position in use.

BRIEF DESCRIPTION OF THE DRAWINGS

With reference to the appended drawings, below follows a closer description of embodiments of the invention cited as examples.

In the drawings.

DETAILED DESCRIPTION OF DIFFERENT EMBODIMENTS OF THE INVENTION

Figure 1:
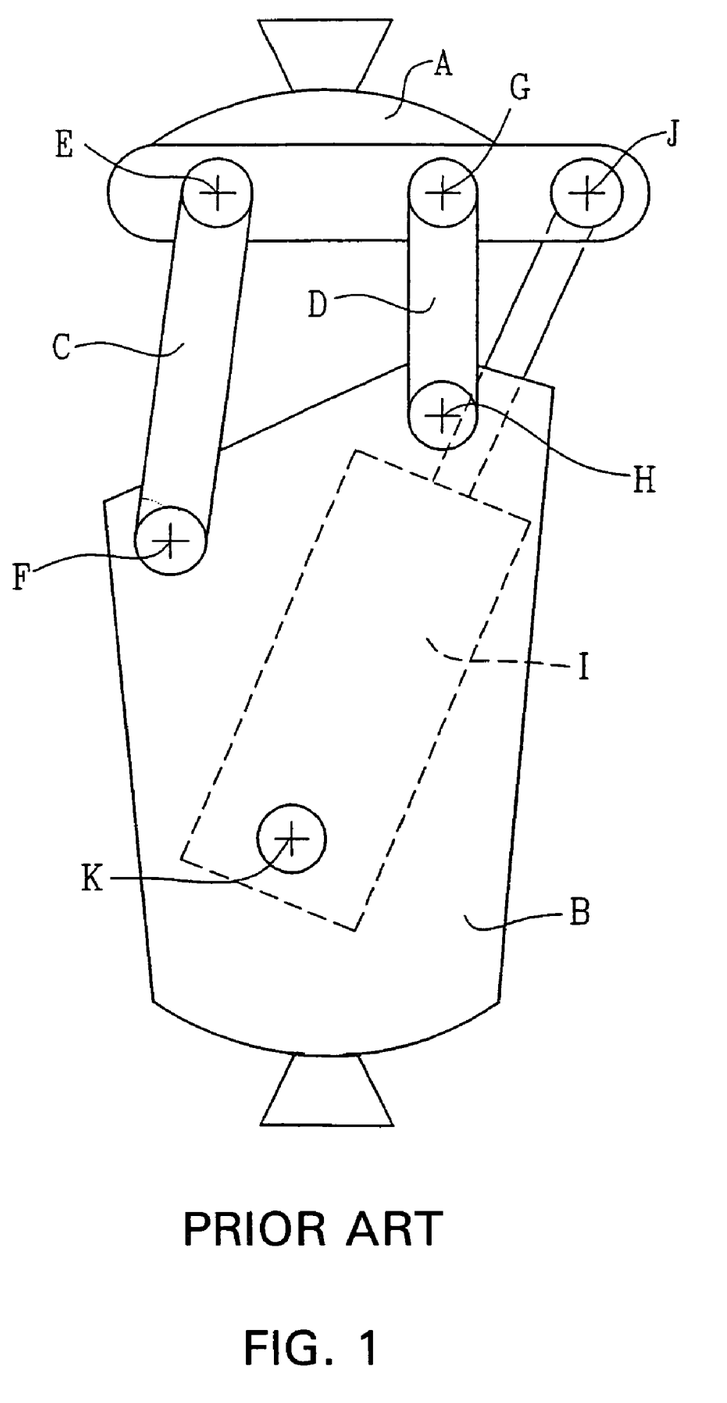
FIG. 1 is a schematic illustration of a four axis knee joint provided with a hydraulic cylinder according to prior art.

In FIG. 1 an artificial knee joint according to prior art is schematically illustrated. The knee joint has an upper leg portion A and a lower leg portion B, and front C and rear D links which are pivotally connected to the upper A and lower B leg portion to obtain a four axis knee joint by means of these links which have four geometrical pivot axes E, F, G, H. Furthermore, the knee joint comprises a hydraulic cylinder I for swing phase control which hydraulic cylinder I is pivotally connected to the upper A and lower B leg portions around two further geometrical pivot axes J, K.

Figure 2A:
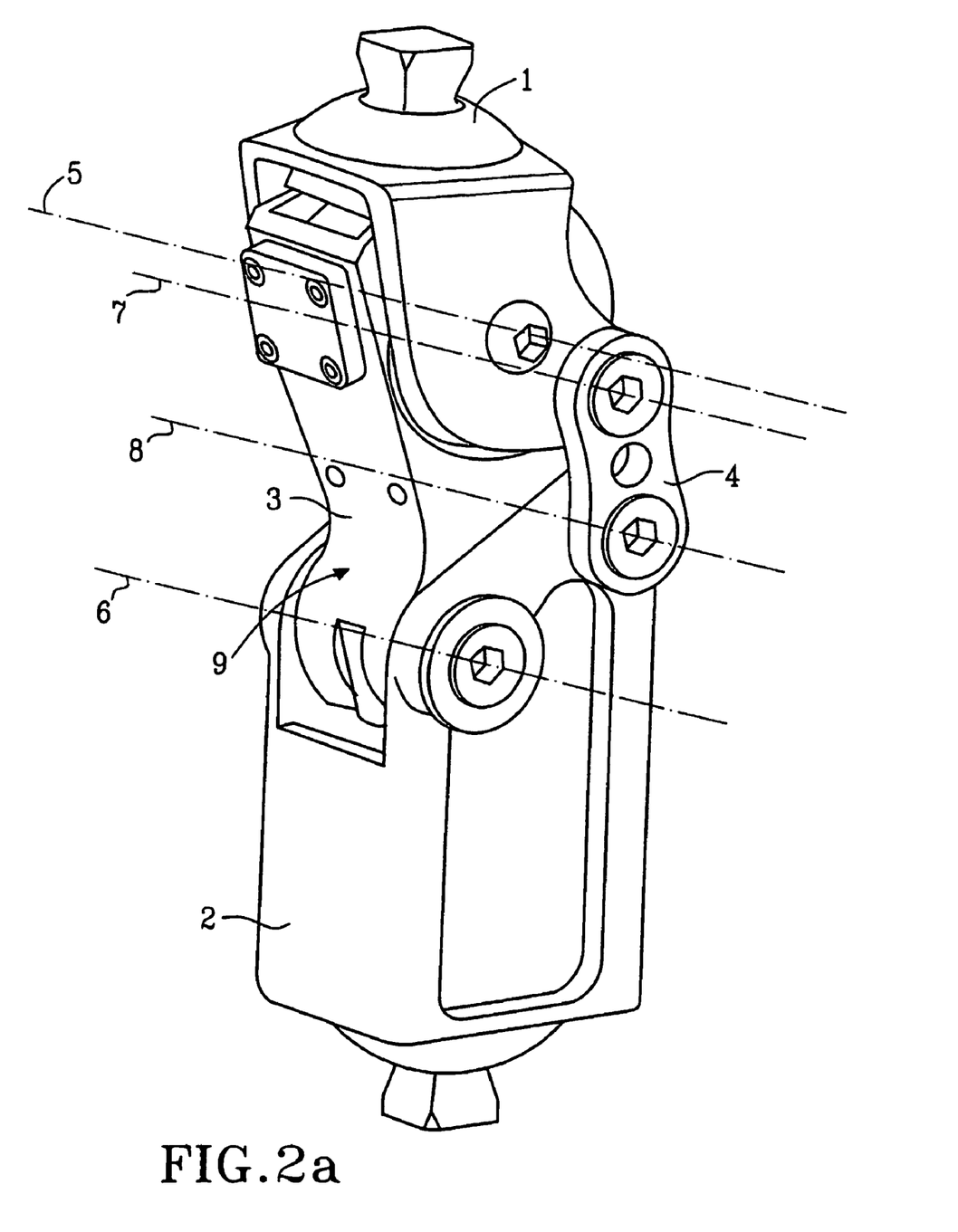
FIG. 2a is a perspective view taken obliquely from the front of a knee joint according to the invention.
Figure 2B:
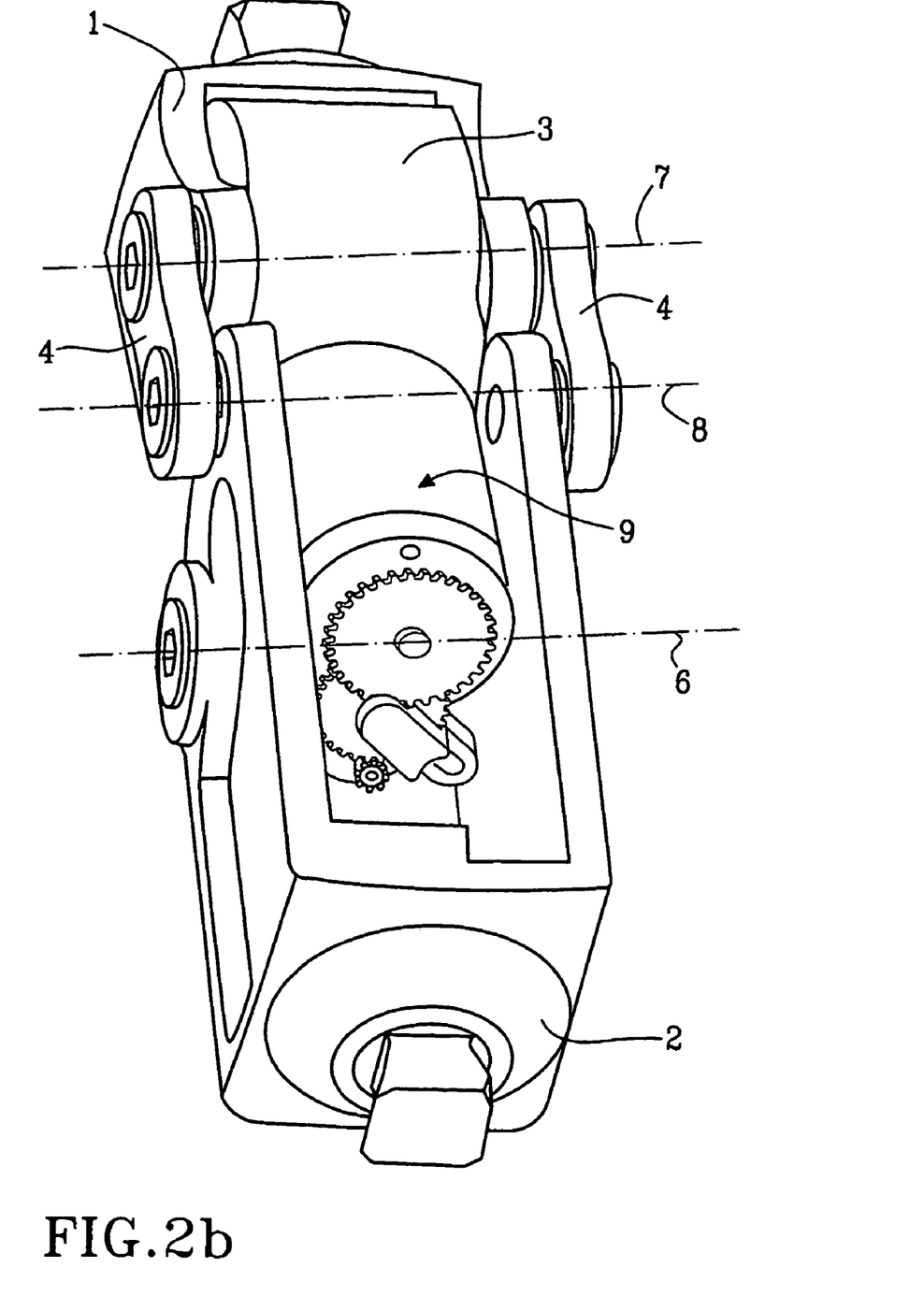
FIG. 2b is a perspective view taken obliquely from behind the knee joint illustrated in FIG. 2a, FIG. 3a is a lateral view of the knee joint illustrated in FIGS. 2a and 2b, the knee joint being in a neutral position, i.e. in a not bent state.

In FIGS. 2a and 2b a knee joint according to the invention is illustrated in perspective views. The knee joint comprises an upper leg portion 1 and a lower leg portion 2. The upper leg portion 1 and the lower leg portion 2 are pivotally connected to each other by means of a front link 3 and at least one rear link 4. In the example illustrated, the knee joint is provided with two such rear links 4. Although it has been shown to be favourable to use one front link and two rear links, the terms "front" and "rear" meaning the relative positions of the links in respect of how the knee joint is directed during use when a user moves forward, it should be emphasised that in another embodiment the knee joint could have for example two front links and one rear link or two front links and two rear links.

The front link 3 is at one end thereof pivotally connected to the upper leg portion 1 for pivoting the front link and the upper leg portion relative to each other around a first geometrical pivot axis 5, and at the other end thereof pivotally connected to the lower leg portion 2 for pivoting the front link and the lower leg portion relative to each other around a second geometrical pivot axis 6. Said at least one rear link 4 is at one end thereof pivotally connected to the upper leg portion 1 for pivoting said at least one rear link and the upper leg portion relative to each other around a third geometrical pivot axis 7, and at the other end thereof pivotally connected to the lower leg portion 2 for pivoting said at least one rear link and the lower leg portion relative to each other around a fourth geometrical pivot axis 8. The front link 3 and said at least one rear link 4 which include said first, second, third, and fourth pivot axes 5, 6, 7, 8 form the pivot centre of the knee joint. Furthermore, in addition to the front link 3 and said at least one rear link 4 the knee joint comprises a further means 9 for controlling the bending characteristics of the knee joint.

The further controlling means 9 can be different types of mechanisms which have different designs for controlling the different bending characteristics of the knee joint. Although other functions of the knee joint is also possible to control, in the example described below the controlling means is arranged for controlling the requisite torque for bending the knee joint around its pivot centre. In the knee joint according to the invention the controlling means 9 is integrated in some of the front link 3 and said at least one rear link 4. In the example illustrated, the controlling means 9 is integrated in the front link 3 and arranged internally in this front link 3 for controlling the torque required for bending the knee joint. By the term "Integrated controlling means 9" it is intended that the controlling means, or at least a substantial part thereof, is arranged on or inside the current link, where the controlling means also could form the current link or a substantial part thereof, and that the controlling means per se does not require any further external geometrical pivot axis in the knee joint than the pivot axes, which axes would have been required by the current link even if the knee joint was not provided with this further controlling means and which provide for that the link will be pivotally connected to the upper and lower leg portions. For example, compare with the prior art illustrated in FIG. 1 where the controlling means, i.e. the hydraulic cylinder I, requires two more external pivot axes J, K in addition to the pivot axes E, F, G, H that the links require for forming the pivot centre of the knee joint. On the other hand, the controlling means 9 according to the invention may have one or more internal pivot axes. By the term "internal pivot axis" is meant a pivot axis for a relative motion between two components which both are arranged in the current link, preferably internally of the current link. An internal pivot axis is thus not arranged to directly connect the current link to any other component, such as another link or the upper or lower leg portions, of the knee joint for achieving a pivot motion between the link and such another component.

Although there follows an embodiment in which the integrated controlling means for controlling the pivot resistance of the knee joint suitably cooperates with an electronic control system, an integrated controlling means according to the invention could be included in a substantially completely mechanical system. However, it should be pointed out that in case an electronic control system is used, some surrounding equipment which makes part of or cooperates with the controlling means, such as sensors, transducers, equipments for signal processing and/or power supply, can very well be arranged on a position other than in the current link.

Figure 3A:
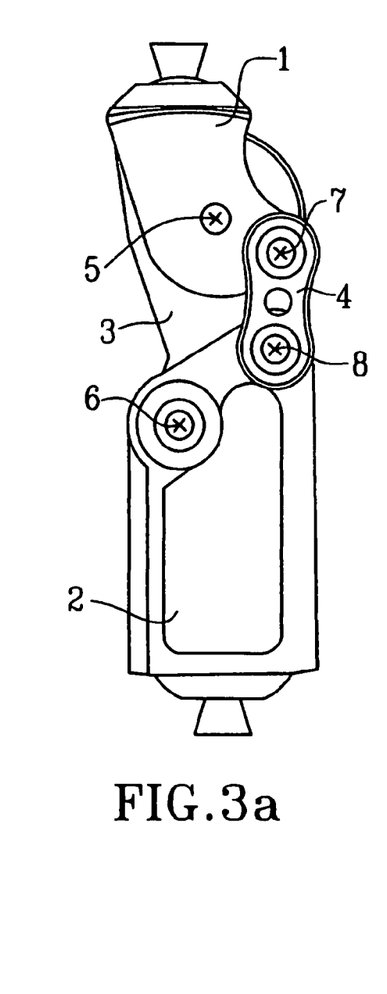
Figure 3B:
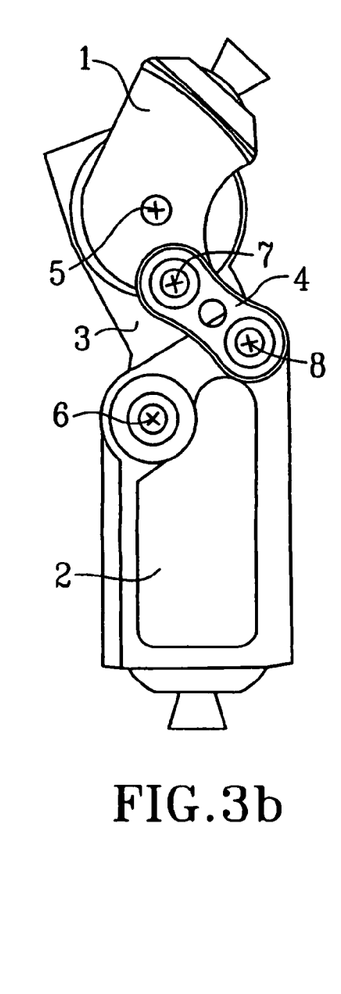
FIG. 3b is a view according to FIG. 3a, the knee joint being bent about 45°.
Figures 3C, 3D:
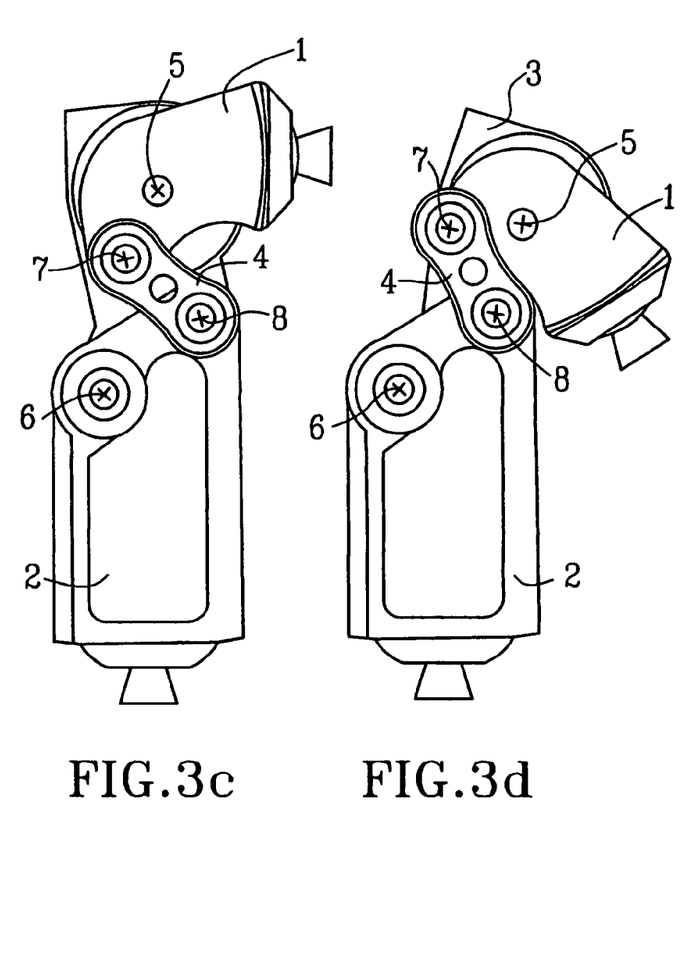
FIG. 3c is a view according to FIG. 3a, the knee joint being bent about 90°.
FIG. 3d is a view according to FIG. 3a, the knee joint being bent about 135°.

In FIGS. 3a-3d the knee joint is illustrated in four lateral views, showing the bending of the knee joint around the pivot axes 5, 6, 7, 8. In these figures, the lower leg portion 2 is fixed only for the sake of clarity, for illustrating how the upper 1 and the lower 2 leg portions move relative to each other when the knee joint is bent. It hereby follows that the position for said second pivot axis 6 and the position for said fourth pivot axis 8 are fixed, whereas the positions of said first pivot axis 5 and said third pivot axis 7 are changed when the knee joint is pivoted around its pivot centre. In FIG. 3a the knee joint is in a neutral position where the upper 1 and lower 2 leg portions are not pivoted relative to each other (which corresponds to the position when a user of the prosthesis has the leg straightened). In FIG. 3b the upper leg portion 1 is pivoted about 45° relative to the lower leg portion 2, in FIG. 3c the upper leg portion 1 is pivoted about 90° and finally in FIG. 3d the upper leg portion 1 is pivoted about 135° relative to the lower leg portion 2.

Figure 4A:
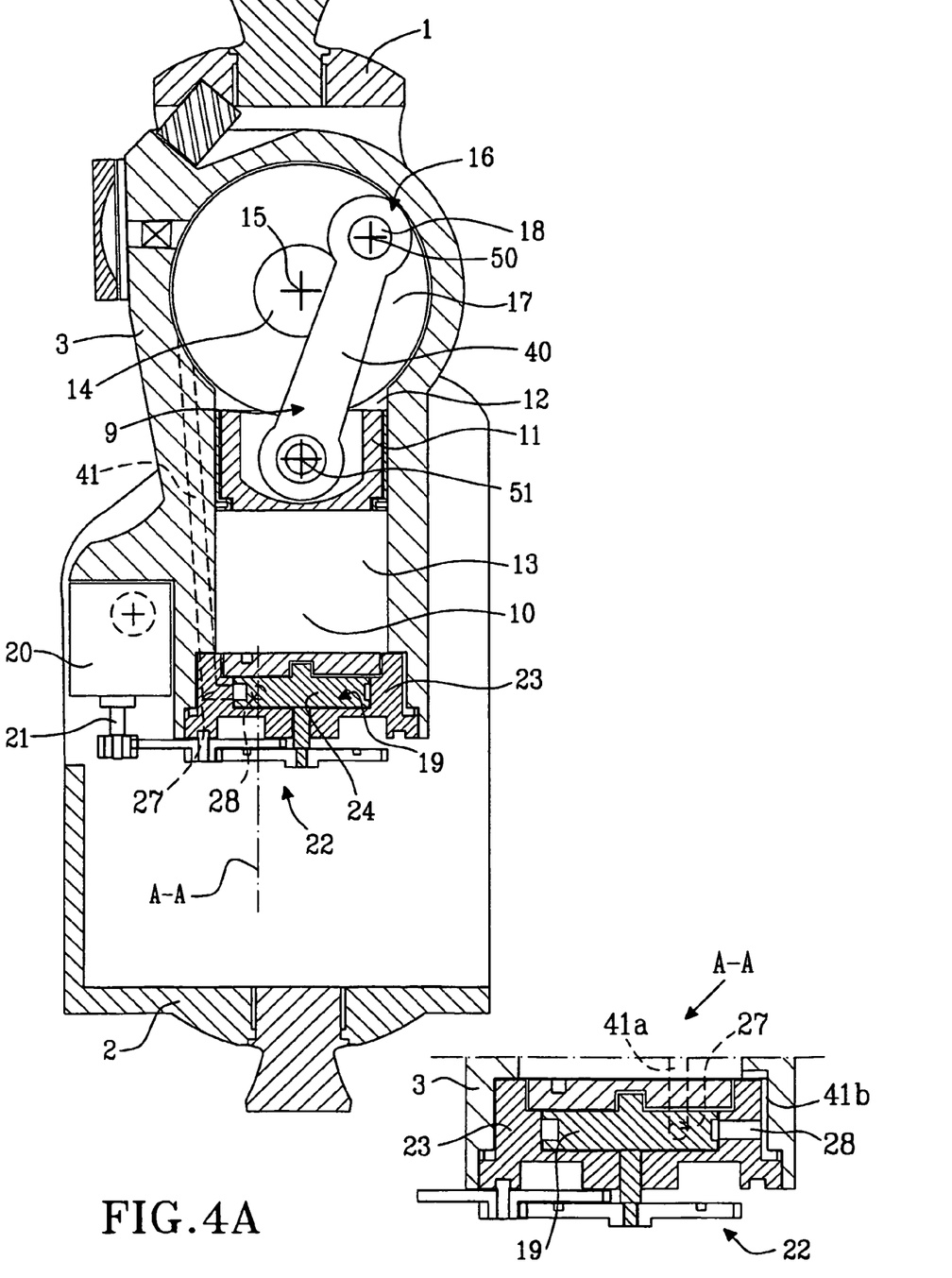
FIG. 4a is a cut view of the knee joint in FIG. 3a, FIG. 4b is a view according to FIG. 4a, the knee joint forming a positive angle.
Figure 4B:
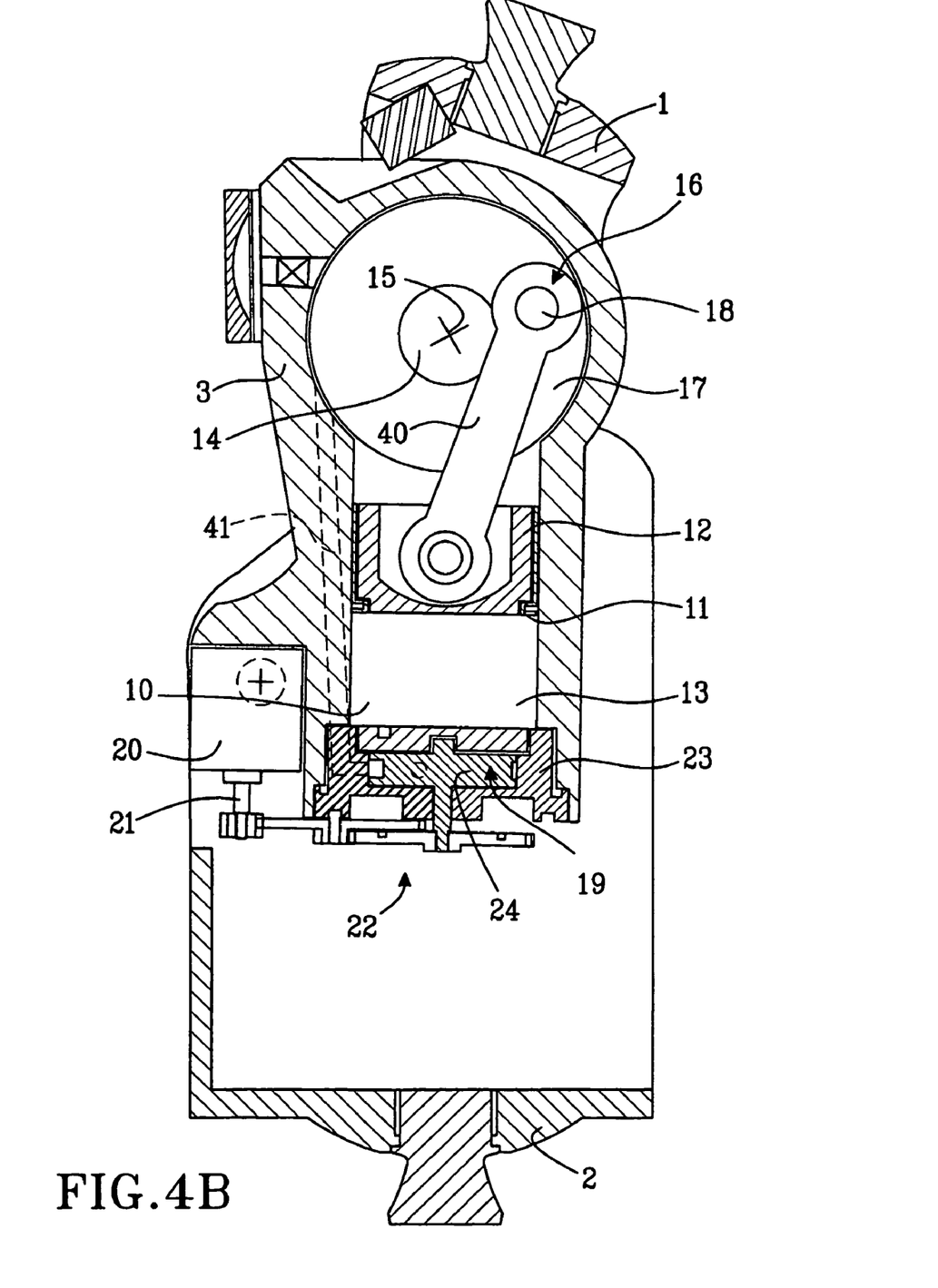
Figure 4C:
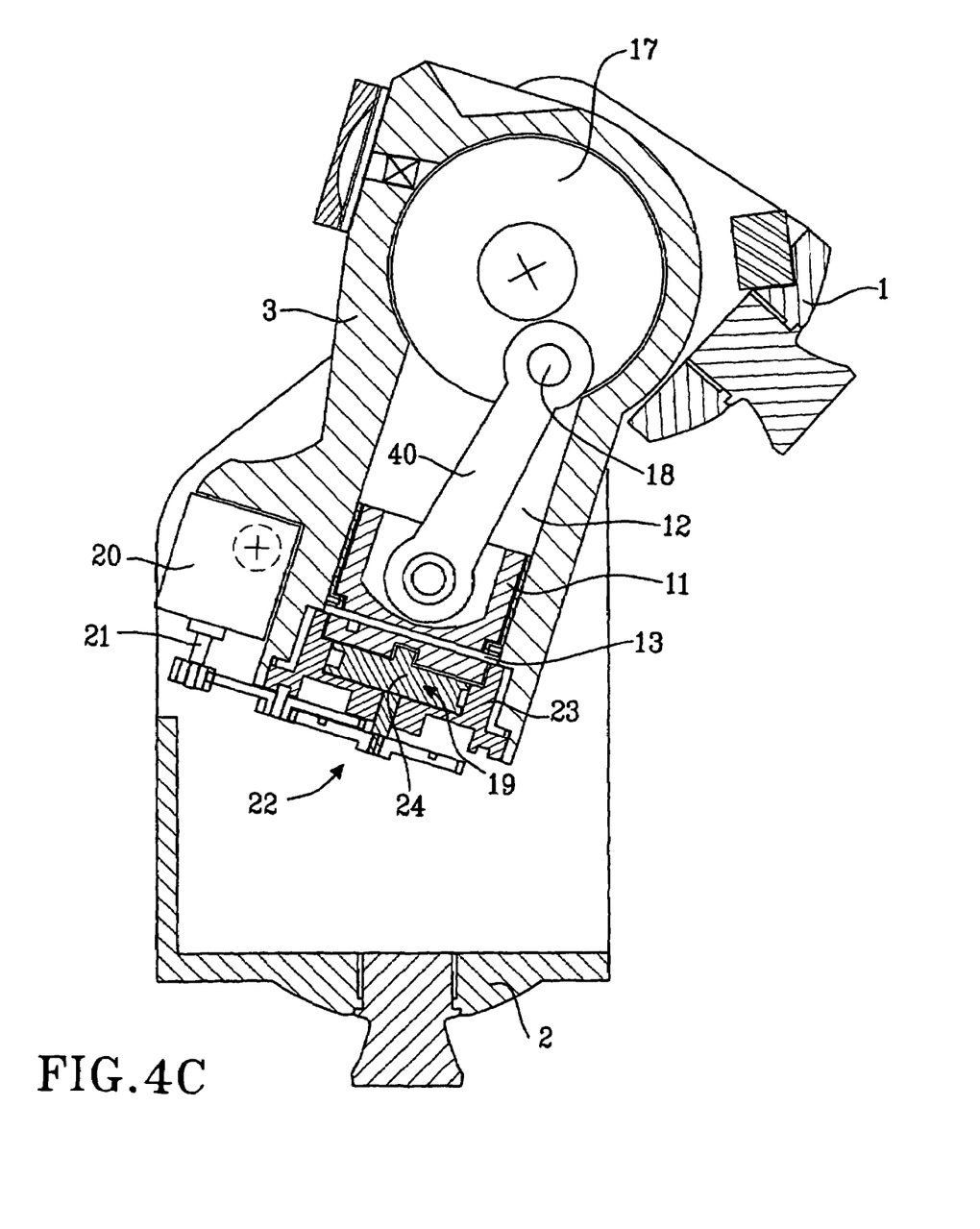
FIG. 4c is a view according to FIG. 4a, the knee joint being maximally bent.

In FIGS. 4a-4c the knee joint according to the invention is shown in cut views. In the embodiment according to FIGS. 4a-4c the controlling means 9 comprises a cylinder 10 integrated in the front link 3 for controlling the requisite torque for bending the knee joint. In the cylinder 10 there is a working fluid, such as for example hydraulic oil, and a piston 11 movably arranged in the cylinder 10 for rectilinear movement in the cylinder. However, it should be emphasised that in another embodiment the controlling means could be pneumatic and in such a case the working fluid would instead be air. The cylinder 10 is provided with a coil pipe 41 for the working fluid which coil pipe 41 connects two chambers 12, 13 formed on each side of the piston. This means that the system is closed in such a way that when the piston 11 is moved in a first direction, the working fluid flows from a first 12 of the chambers to the second chamber 13, and when the piston 11 is moved in the other direction, the working fluid flows in the opposite direction from said second chamber 13 to said first chamber 12.

The invention may advantageously be applied together with a single valve system, i.e. a control arrangement based on only one valve arranged for varying the pivot resistance which is achieved by means of the controlling means 9. The use of only one valve in the controlling means 9 results in a simple design which simplifies the control functions which are required for controlling the pivot resistance of the knee joint and for giving the knee joint the desired characteristics. By means of a valve which can be opened and closed for controlling the flow of the working fluid in a first direction, when the working fluid is transported from the first chamber 12 to the second chamber 13, and in a second direction, when the working fluid is transported from the second chamber 13 to the first chamber 12, the pivot resistance of the knee joint can be controlled within a given interval for the both pivot directions of the knee joint. Such control may be varied substantially infinitely within the given interval.

In a cut view A-A in FIG. 4A, a first part 41a of the coil pipe 41 which connects the first (upper) chamber 12 to a valve 19, and a second part 41b which connects the valve 19 to the second (lower) chamber 13 are shown.

A first leg portion of the upper and the lower leg portions, here the upper leg portion 1, is arranged to transmit a relative pivot motion of this first leg portion and the other of the upper and lower leg portions, here the lower leg portion 2, to a rectilinear motion of the piston 11 in the cylinder 10 during bending of the knee joint, by means of a crank shaft 14. This means that the requisite torque for bending the knee joint is a function of the force required to move the piston 11 in the cylinder 10.

In the example illustrated, the rotation axis 15 of the crank shaft 14 is arranged along the first geometrical axis 5 and connected to the upper leg portion 1 such that the crank shaft 14 is pivoted when pivoting the upper leg portion 1 relative to the lower leg portion 2. Furthermore, the crank shaft 14 has in the second end thereof an eccentric 16, such as a disk 17 provided with a shaft pivot 18 which is arranged for interconnecting the crank shaft 14 and the piston rod 40 of the piston 11, which means that during bending the knee joint around its pivot centre also the eccentric 16 will be pivoted and thus, the piston 11 will be moved in the cylinder 10. Pivot axes 50, 51 between the disk 17 and the piston rod 40 and between the piston rod 40 and the piston 11, respectively, constitute internal pivot axes according to the previously given definition.

Figure 7:
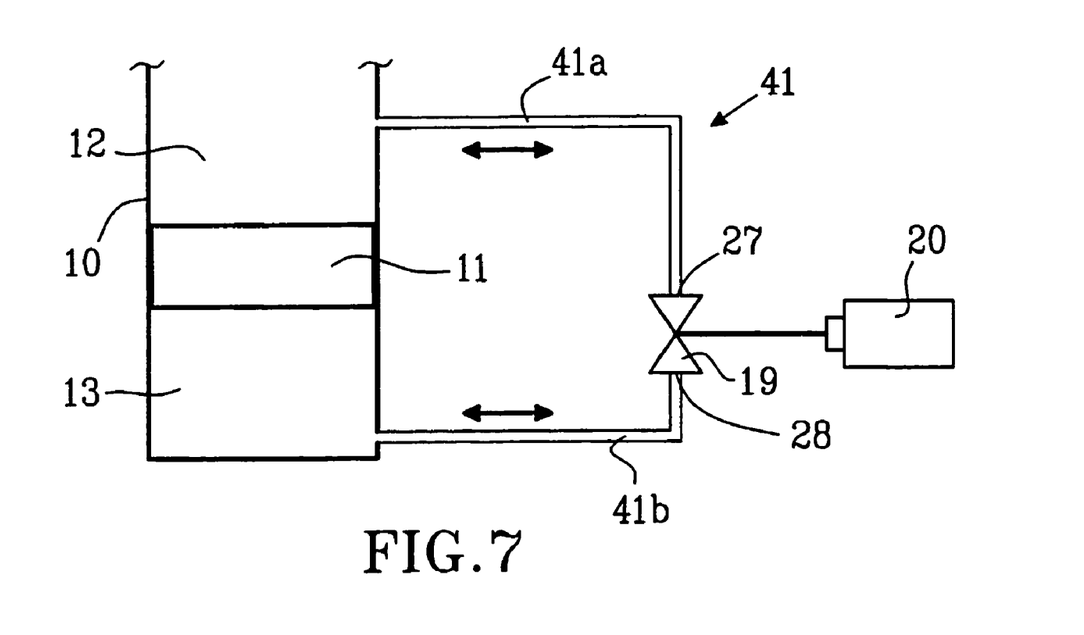
FIG. 7 is a schematic illustration of cooperation between different components of a controlling means in one embodiment of the knee joint according to the invention.

The resistance which has to be overcome to move the piston 11 can in turn be controlled by means of the valve 19 arranged in said coil pipe 41 for regulating the flow of the working fluid in the coil pipe 41. By providing the coil pipe with the valve 19 for regulating the flow of the working fluid in the coil pipe 41, the requisite torque for bending the knee joint may thus be controlled. The controlling means 9 may further comprise a motor 20 for adjustment of the valve 19. This is also schematically illustrated in FIG. 7 where the cylinder 10 having said both chambers 12, 13 and the piston 11 are shown together with the coil pipe 41, the valve 19 and the motor 20.

Figures 5, 6:
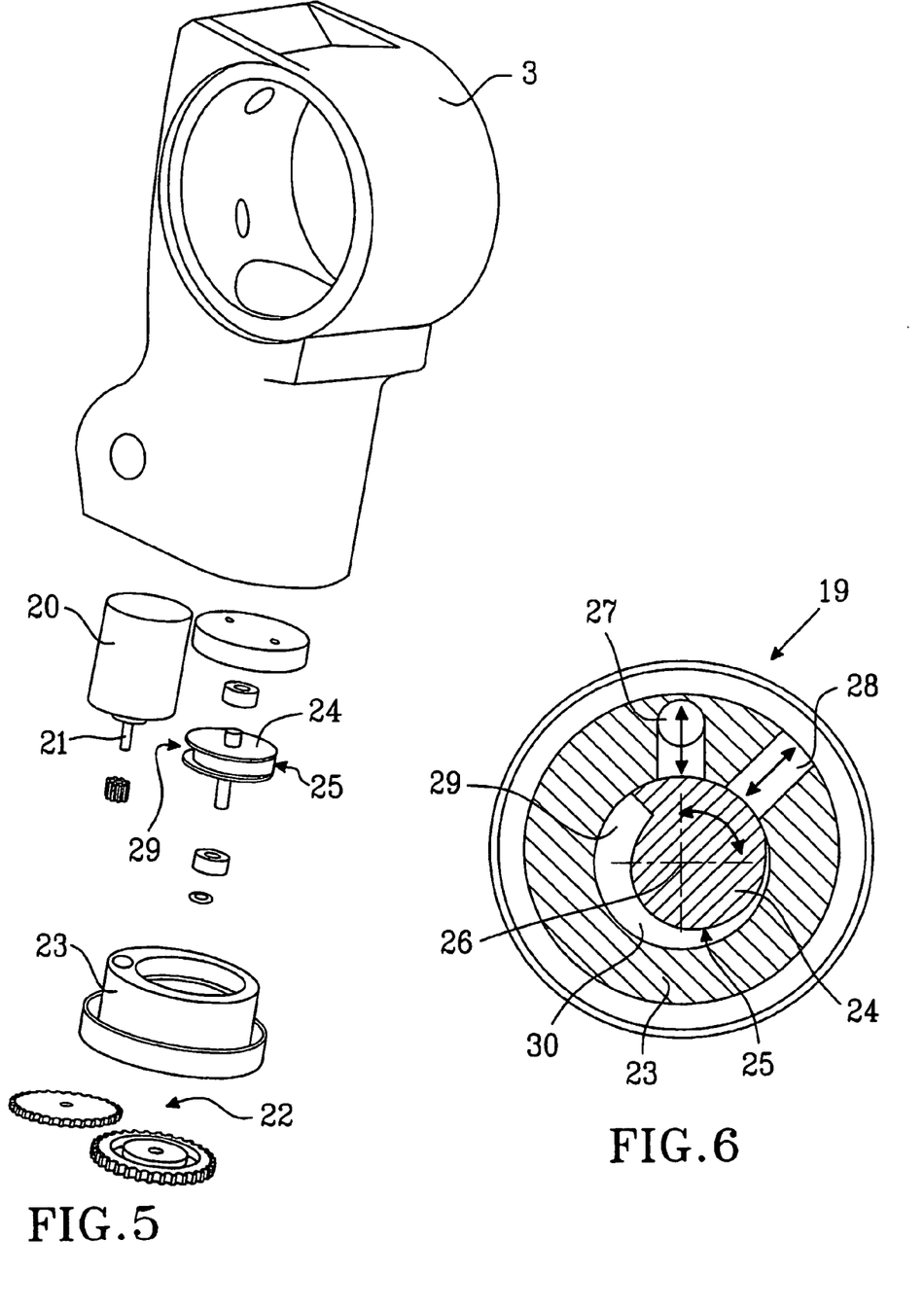
FIG. 5 is an exploded view having components of a controlling means in one embodiment of the knee joint according to the invention.
FIG. 6 is a cut view of the valve disk according to FIGS. 4a-4c and 5, the disk being viewed in the axial direction with respect to the geometrical pivot axis thereof.

In the embodiment illustrated, the controlling means 9 thus comprises a valve 19 and a motor 20 for adjustment of the valve 19. However, it should be emphasised that in another embodiment, for example the valve and the motor where appropriate, could be arranged in another position different from the front link. In this case, the main part of the controlling means, i.e. the cylinder with the piston, would be arranged in the front link such as previously described and furthermore the cylinder would suitably be connected to the valve by means of hoses or similar. The motor 20, which in the illustrated embodiment has the motor shaft 21 arranged in parallel with the extension in the length direction of the cylinder 10, is arranged to drive a disk 24 via a gear 22, which disk is pivotably arranged in the valve housing 23, the pivot position of which relative to the valve housing 23 determines the percentage opening of the valve 19 and thus regulates the flow in the coil pipe. The disk 24 has a radially directed periphery surface 25, the distance of which relative to the geometrical pivot axis 26 of the disk varies along the circumference of the disk, see FIG. 5, which is a exploded view illustrating the different components of the controlling means 9 and FIG. 6 which illustrates the disk 24 in a cut view looked on in the axial direction in respect of the geometrical pivot axis 26 thereof.

Preferably, the contour of the disk 24 along the circumference thereof as regards said periphery surface 25 has the shape of an involute. As shown more in detail in FIGS. 5 and 6, by such a disk 24 cooperating with a cylindrical space of the valve housing 23, and with an inlet 27 and an outlet 28 of the valve housing 23, the percentage opening of the valve may be varied infinitely in the interval from totally closed to completely opened. The disk 24 is provided with groove 29 along the periphery of the disk. The depth of the groove 29 increases gradually along the periphery from zero to a maximum value and then returns to zero again in a single jump. When the position of the disk 24 so allows, the working fluid can flow from the inlet 27, into the groove 29 of the disk 24 and further out through the outlet 28. The inlet 27 and the outlet 28 are in communication with a respective chamber 12, 13 of the cylinder 10 for forming the coil pipe 41. Depending on the position of the disk 24 relative to the valve housing 23, i.e. relative to the inlet 27 and the outlet 28, different throttling of the working fluid will be provided because the size of the cross section surface of the streaming channel 30 for the working fluid formed between the periphery surface 25 and the valve housing 23 is changed if the position of the disk 24 is changed. Although the two apertures of the valve housing are called inlet 27 and outlet 28 above, of course these work both as inlet and outlet, and when the working fluid of the cylinder flows in one direction one aperture can be regarded as an inlet and the other aperture as an outlet to the streaming channel 30, whereas during flow of the working fluid in the opposite direction the first aperture can be regarded as an outlet and the second aperture as an inlet to the streaming channel 30.

To provide a knee joint which imitates a human knee joint as closely as possible regarding the function in use, i.e. enables a "normal" walk, it is desired that the resistance against pivoting around the pivot centre of the knee joint may be varied during different parts of the cycle when the leg is to be moved for the purpose of supporting on the leg, walking or running. By means of a control unit, the motor may be controlled so that a natural and gentle leg motion is obtained.

Of course in addition to those described herein, there are other ways to design the device according to the invention within the framework of the invention, and it is emphasised that the scope of protection of the invention is restricted only by the following claims. For example, instead of a hydraulic cylinder, a pneumatic cylinder could be used as controlling means for the bending characteristics of the knee joint. Another possible controlling means for controlling the bending characteristics of the knee joint which could be integrated according to the invention is an arrangement based on rotary hydraulics.

The invention claimed is:

1. An artificial multi-axis knee joint comprising an upper leg portion (1) and a lower leg portion (2), said upper leg portion and said lower leg portion being pivotally connected to each other by means of a front link (3), which front link (3) at one end thereof is pivotally connected to the upper leg portion (1) for pivoting the front link and the upper leg portion relative to each other around a first geometrical pivot axis (5) and at the other end thereof is pivotally connected to the lower leg portion (2) for pivoting the front link and the lower leg portion relative to each other around a second geometrical pivot axis (6), and by means of at least one rear link (4), which rear link (4) at one end thereof is pivotally connected to the upper leg portion (1) for pivoting said at least one rear link and the upper leg portion relative to each other around a third geometrical pivot axis (7) and at the other end thereof is pivotally connected to the lower leg portion (2) for pivoting said at least one rear link and the lower leg portion relative to each other around a fourth geometrical pivot axis (8), in addition to the front link (3) and said at least one rear link (4) the knee joint further comprising a further means (9) for controlling the bending characteristics of the knee joint, wherein the controlling means (9) is integrated in one of the front link (3) and said at least one rear link (4);

wherein the controlling means (9) is arranged internally of the front link (3) or said at least one rear link (4);

wherein the controlling means (9) includes pivot axes consisting of the first and second geometrical pivot axes.

2. Knee joint according to claim 1, wherein the controlling means (9) is integrated in the front link (3).

3. Knee joint according to claim 1, wherein the controlling means (9) is arranged to control the requisite torque for bending the knee joint.

4. Knee joint according to claim 3, wherein the controlling means (9) comprises a cylinder (10) having two chambers (12, 13), a working fluid and a piston (11) movably arranged in the cylinder for controlling the requisite torque for bending the knee joint.

5. Knee joint according to claim 4, wherein the upper leg portion (1) is arranged to transmit a relative pivot motion of the upper leg portion (1) and the lower leg portion (2) is arranged to transmit a rectilinear motion of the piston (11) in the cylinder (10) during bending of the knee joint, by means of a crank shaft (14).

6. Knee joint according to claim 5, wherein the rotation axis (15) of the crank shaft (14) extends along said first geometrical pivot axis (5) of the front link (3) at said upper leg portion (1).

7. Knee joint according to claim 6, wherein the cylinder (10) is pivotally connected to said lower leg portion (2) for pivoting the cylinder (10) and said lower leg portion (2) relative to each other around said second geometrical pivot axis (6) of said front link (3).

8. Knee joint according to claim 4, wherein the cylinder (10) is provided with a coil pipe (41) for the working fluid which coil pipe connects both chambers (12, 13) of the cylinder on each side of the piston (11).

9. Knee joint according to claim 8, wherein said coil pipe (41) is provided with a valve (19) for regulating the flow of the working fluid in the coil pipe and controlling the requisite torque for bending the knee joint.

10. Knee joint according to claim 9, wherein the controlling means (9) comprises a motor (20) for operating the valve (19).

11. Knee joint according to claim 10, wherein the motor (20) is arranged to drive the valve disk (24) and to pivot this disk for operating the percentage opening of the valve (19).

12. Knee joint according to claim 9, wherein the valve (19) comprises a valve housing (23) and a disk (24) pivotably arranged in the valve housing, the pivot position of which relative to the valve housing (23) determines the percentage opening of the valve (19) and thus regulates the flow in the coil pipe.

13. Knee joint according to claim 12, wherein the disk (24) has a radially directed periphery surface (25) the distance of which relative to the geometrical pivot axis of the disk (24) varies along the circumference of the disk.

14. Knee joint according to claim 13, wherein the contour of the disk along the circumference thereof as regards said periphery surface (25) has the shape of an involute.

15. Knee joint according to claim 9, wherein the knee joint is provided with only one valve (19) for controlling the requisite torque for bending the knee joint by means of the controlling means (9).

16. Knee joint according to claim 1, wherein the knee joint has a total of four said external pivot axes (5, 6, 7, 8) for forming the geometrical pivot centre of the knee joint and arranging said controlling means (9).

17. Knee joint according to claim 1, wherein the knee joint has two rear links (4) arranged spaced apart from each other which both are pivotally connected to the upper leg portion (1) and the lower leg portion (2) for pivoting around the third (7) and fourth (8) geometrical pivot axis, respectively.

* * * * *